United States Patent [19]

Farrar et al.

[11] Patent Number: 4,950,788

[45] Date of Patent: Aug. 21, 1990

[54] PROCESS FOR PRODUCING UNSATURATED CARBOXYLIC ACIDS

[75] Inventors: David Farrar; Peter Flesher, both of West Yorkshire, England

[73] Assignee: Allied Colloids Limited, United Kingdom

[21] Appl. No.: 314,544

[22] Filed: Feb. 23, 1989

[30] Foreign Application Priority Data

Feb. 25, 1988 [GB] United Kingdom ............... 8804424

[51] Int. Cl.$^5$ ............................................. C07C 57/02
[52] U.S. Cl. .................................... 562/598; 562/526; 560/215; 564/129; 564/130; 564/131
[58] Field of Search ................ 562/598, 526; 564/130, 564/131, 129; 560/215

[56] References Cited

U.S. PATENT DOCUMENTS 2,890,101 6/1959 Borrel .................................. 423/520
3,956,387 5/1976 Dockner ............................. 564/127

FOREIGN PATENT DOCUMENTS 9135917 12/1974 Japan.
4015 1/1975 Japan.

OTHER PUBLICATIONS

CA 86:71925A, 1976.
CA 99:71293C, 1981.
CA 91:158321U, 1979.
CA 83:79933B, 1974.
CA 44010W, 1975.
CA 72:89793T, 1970.
CA 55:2485G, 1959.
CA 92:93905K, 1979.
CA 87:185002Q, 1977.
CA 86:89183H, 1976.

Primary Examiner—Paul J. Killos
Assistant Examiner—Steven B. Jervey
Attorney, Agent, or Firm—Ostrolenk, Faber, Gerb & Soffen

[57] ABSTRACT

Acrylic acid or other unsaturated carboxylic acid is made by hydrolysing the corresponding nitrile in the presence of excess sulphuric acid to form amide sulphate, adding amide in an amount such that the total amount of amide and nitrile fed to the process is greater than 1 mole per mole sulphuric acid, hydrolysing the amide sulphate and amide to the desired acid and separating the acid from the sulphate by-products.

15 Claims, No Drawings

PROCESS FOR PRODUCING UNSATURATED CARBOXYLIC ACIDS

This invention relates to a process for producing an unsaturated carboxylic acid, by hydrolysis of a corresponding nitrile. For instance (meth) acrylonitrile can be hydrolysed by the process to (meth) acrylic acid.

It is well known that unsaturated nitriles and unsaturated amides can be hydrolysed by reaction with water in the presence of a hydrolysis reagent to form unsaturated acids.

In Chemical Abstracts 72:89793T a nitrile is hydrolysed in an acid salt melt containing water, the melt being formed in an example of 24 parts potassium bisulphate, 28 parts sodium bisulphate and 1 part ammonium sulphate. Handling the melt is inconvenient and normal processes are conducted in aqueous solution. Thus in Chemical Abstracts 86:89183H an amide or nitrile is hydrolysed in an aqueous solution of an ammonium salt as the hydrolysis reagent. In particular, the use of ammonium sulphate gave 32% conversion of acrylamide and other ammonium salts that were used were ammonium chloride, bromide, bisulphate and nitrate. In Chemical Abstracts 92:93905K tin IV compounds are used as the hydrolysis reagent. In Chemical Abstracts 86:71925A a Be salt is used.

Despite these various proposals, sulphuric acid has become accepted as being particularly suitable for use as the hydrolysis reagent. For instance in Chemical Abstracts 55:2485G 1 mole acrylonitrile is reacted with 1 mole sulphuric acid and 2 moles water. The conversion of a nitrile to the acid by this reaction goes in two stages, with the formation in the first stage of an amide sulphate and the hydrolysis of this in the second stage to the carboxylic acid, with ammonium bisulphate as a by-product.

It has been well accepted that it is desirable to use excess sulphuric acid, in order that the reaction proceeds at a satisfactory rate and yield. For instance Chemical Abstracts 87:185002Q reports an investigation on the kinetics and recommends 1.17 moles sulphuric acid per mole methacrylamide, and 1.5 to 2.5 moles sulphuric acid per mole acrylamide sulphate are used in Chemical Abstracts 99:71293C.

It is necessary to separate the (meth) acrylic acid or other desired product from the reaction mixture containing ammonium bisulphate and it can be difficult to achieve perfect separation. In Chemical Abstracts 83:79933B and Japanese Unexamined Application 49-135917the reaction mixture is subjected to phase separation to separate a methacrylic acid-rich layer from a layer containing 40 to 50% sulphuric acid, 10 to 20% ammonium bisulphate, 30 to 40% water, 1 to 2% methacrylic acid and 0.4 to 0.6% methacrylamide. This layer is distilled to recover the small amount of methacrylic acid and methacrylamide, which is recycled back to the hydrolysis stage. This recycled acrylamide will thus constitute a very small amount of the total charge in that stage.

In Chemical Abstracts 91:158321U acetone cyanohydrin is reacted in aqueous solution with more than 1 mole sulphuric acid to form acrylamide sulphate in the presence of unreacted sulphuric acid, and further water is added and the mixture hydrolysed to form methacrylic acid. In Chemical Abstracts 83:44010W a similar process is described starting from methacrylonitrile, with the final product being subjected to phase separation and recycling of the small amount of distillate.

Although processes that start from nitrile and excess sulphuric acid can be operated conveniently to give a good yield of acrylic acid or other unsaturated acid end product they suffer from a number of disadvantages. In particular, they produce a large volume of ammonium bisulphate as a by-product. The inconvenience of producing these large quantities is increased by the fact that it is contaminated with a significant amount of sulphuric acid. It is therefore necessary either to dump large volumes of this by-product (which is environmentally difficult) or to convert it to a usable material, for instance by reaction with aqueous ammonia to form ammonium sulphate, which can then be used as a fertiliser. However the amount of ammonia that is required is very high, due partly to the presence of the sulphuric acid.

Another difficulty is that the presence of free sulphuric acid tends to result in significant levels of sulphur dioxide in the final acrylic acid or other carboxylic acid stream, and this is undesirable. Another difficulty is that it is, in conventional manner, necessary to include a polymerisation inhibitor throughout the reaction but the excess sulphuric acid tends to interact with the inhibitor and so large amounts of the inhibitor, which is generally rather expensive, have to be added in order to maintain adequate levels of inhibition.

It would be desirable to minimise these problems whilst maintaining the good reaction rates and yields associated with the use of excess sulphuric acid as the hydrolysis reagent.

In the invention, an ethylenically unsaturated acid of the formula $R^1C=CR^2COOH$, in which $R^1$ is H, alkyl or aryl and $R^2$ is H or $CH_3$, is made from the corresponding nitrile by a process comprising feeding the nitrile to a reaction vessel and reacting it in aqueous solution in that vessel with water in the presence of an amount of sulphuric acid that is above 1 mole per mole nitrile and thereby forming a first reaction product containing the corresponding amide sulphate, feeding the corresponding amide to the first reaction product in an amount such that the total amount of amide and nitrile fed to the process is above 1 mole per mole sulphuric acid, hydrolysing the amide and amide sulphate by reaction in aqueous solution with water and thereby forming the corresponding acid and a sulphate by-product, and separating the corresponding acid from the sulphate by-product.

In the final acid, $R^1$ may be hydrogen, alkyl (usually C1-8 and preferably methyl) or aryl, preferably phenyl. $R^2$ may be hydrogen or methyl. By referring to the "corresponding" amide and nitrile we mean that the values of $R^1$ and $R^2$ in the nitrile, amide and amide sulphate are such that the desired values of $R^1$ and $R^2$ are obtained in the final acid. Generally the values of $R^1$ and $R^2$ in the nitrile, amide, amide sulphate and acid are identical. However it is also possible to start with, for instance, a nitrile that is saturated but which will form the desired unsaturated acid as a result of desaturation occurring during the process. For instance acetone cyanohydrin is a saturated nitrile but will behave during the process as methacrylonitrile due to the end group being desaturated, to reveal the methacrylic group, during the process. The most preferred process uses acrylonitrile and acrylamide or methyacrylonitrile and methacrylamide as the starting materials for the production of acrylic or methacrylic acid. The preferred process uses acrylonitrile and acrylamide to make acrylic acid.

The amount of sulphuric acid in the first stage must be an excess over the amount of acrylonitrile in order to force the reaction to a satisfactory yield. Generally it is at least 1.05 moles sulphuric acid (per mole nitrile). There is no critical upper limit on the amount of sulphuric acid but increasing the amount does increase the amount of sulphate by-product, and so it is desirable to avoid too large an excess. Generally there is no advantage in using more than 1.5 moles and best results are usually obtained with around 1.1 to 1.3 moles, preferably about 1.2 moles, per mole nitrile.

The amount of amide that is added to the reaction product must be such that the sulphate by-product is substantially free of sulphuric acid and thus the total amount of nitrile and amide fed into the process is preferably at least 1.01 moles per mole sulphuric acid that is fed into the process. If too much amide is added then again this increases the amount of by-product, increases the amount of ammonium sulphate and the consequential risk of crystallisation, and it also has the disadvantage of tending to slow down the reaction and of making it more difficult to separate the carboxylic acid from the amide and other by-products. The total amount of nitrile and amide is therefore usually not more than 1.7 moles, preferably not more than 1.5 moles, per mole sulphuric acid. Generally it is in the range 1.1 to 1.5 moles. It is generally preferred that the amount of amide should be from about 0.05 to 0.5, preferably about 0.1 to 0.4, moles above the difference between the molar proportions of sulphuric acid and nitrile. Thus when, as is often preferred, the amount of sulphuric acid is 1.2 moles per mole nitrile, the difference between the molar proportions of sulphuric acid and nitrile is about 0.2 and the preferred amount of amide is then about 0.3 to 0.6 moles, most preferably about 0.4 moles.

It is very surprising that, contrary to all the suggestions in the literature, it is possible to obtain very good conversion of nitrile in aqueous solution to acid, through the amide sulphate, even though the overall process is deficient in sulphuric acid.

The process has a number of major advantages. One is that the total amount of by-product is less, per mole of carboxylic acid produced, than is obtained in the absence of amide addition. Another is that the by-product is not only produced in a smaller amount but is also more convenient to handle and use. In particular, in the conventional process the by-product consisted almost entirely of ammonium bisulphate and sulphuric acid whereas now it consists substantially of ammonium bisulphate and sulphate, and is substantially free of sulphuric acid. It is therefore more convenient to handle, is environmentally less sensitive, and has a lower ammonia demand if, as is often preferred, it is desired to convert it entirely to ammonium sulphate by reaction with aqueous ammonia.

Furthermore the absence of free sulphuric acid in the second reaction mixture reduces the likelihood of sulphur dioxide being formed by reaction of sulphuric acid with other components in the process. There is less tendency for sulphur dioxide to be driven off with and contaminate the acid product.

Free sulphuric acid also tends to react with the preferred polymerisation inhibitors, (paramethoxyphenol or methylene blue) during the reaction, so that in the process of the invention less of the inhibitor needs to be added (as compared to the conventional process) to produce the same amount of inhibitor in the final product (in the case of paramethoxyphenol) and throughout the reaction. This saving on inhibitor further increases the efficiency of the process.

In the first step of the process, excess sulphuric acid is used in order to drive the reaction to the intermediate amide sulphate as fast as possible. Amide is then added in an amount which exceeds the excess of sulphuric acid from the first step, the resultant mixture is then hydrolysed and the product acid removed. Since free sulphuric acid is not present in this second stage of the reaction, it seems that the hydrolysis is being promoted by the by-product of the reaction, probably ammonium bisulphate.

The by-product of the reaction comprises a mixture of ammonium sulphate and ammonium bisulphate, the proportions of which depend upon the relative quantities of nitrile, amide and sulphuric acid used in the reaction.

The by-product is preferably removed from the reactor as an aqueous solution of its components. Ammonium bisulphate is relatively soluble in water but the other by-product ammonium sulphate is not highly soluble at low temperatures. Since it is preferred to store the by-products for further use or disposal as solutions, it may therefore be necessary to store them at raised temperatures and/or to dilute them with additional water. In general it is preferred that the solids content of the by-product solution is diluted to a concentration of less than 90% by weight, more preferably less than 80 or 70% by weight of the total solution. Since ammonium sulphate is much less soluble than ammonium bisulphate it is preferable that the amount of ammonium sulphate, based on the total of ammonium bisulphate and ammonium sulphate, is less than 50% by weight, although advantageously at least 5 or 10% by weight.

The temperature of reaction of sulphuric acid, water and nitrile in the first step, for instance when the starting material is acrylonitrile, is preferably maintained in the range 90° C. to 100° C., more preferably 95° C. to 98° C., when the pressure is approximately atmospheric. Sufficient water should be present to allow the hydrolysis to proceed. There can be excess but it is usually satisfactory to have an amount of water that is substantially equimolar to the amount of nitrile.

In the second stage, the water for the hydrolysis reaction may all be provided in the form of solvent for the reaction product from the first stage and/or solvent for the amide that is added to the reaction product, or may be added as liquid water. Preferably however some at least of the water is generally supplied as steam to the reactor vessel, suitably below the surface of the liquid in the reactor vessel. The steam may also serve to help drive the acrylic acid product from the reaction mixture. Thus excess steam may be blown through the first reaction product in an amount such that some of the steam passes through the product and strips the corresponding acid from the mixture.

It may be advantageous to aid removal of the acrylic acid by the application of further steam into the vapour space above the liquid in the reactor vessel.

For optimum reaction and removal of acrylic or other acid as the product, the temperature in the reactor vessel should be kept within the range 160° C. to 190° C., preferably in the range 165° C. to 175° C. when the pressure is approximately atmospheric. At lower temperatures acrylic acid as the product is not distilled completely from the mixture and is removed with the liquid by-products. At higher temperatures it becomes difficult to prevent polymerisation of the ethylenically unsaturated compounds present in the reaction mixture.

Although the reaction steps may be carried out at pressures other than atmospheric pressure, it is in general found to be satisfactory to operate around atmospheric pressure. Sometimes it may be useful to increase the pressure with a consequential rise in temperature, e.g. in the first step, to speed up the reaction. Sometimes it may be advantageous to operate the hydrolysis reaction at a reduced pressure in order to aid removal of the acid and/or to allow the acid to be removed at a temperature of which polymerisation is minimised.

Both steps of the reaction process are exothermic. In order to keep the reaction temperature in the second step down in the conventional process it was often necessary to add water to the reactor. A further advantage of the present invention is that that any such water has effectively been replaced by amide solution.

The hydrolysis and steam stripping of the amide sulphate and amide mixture is preferably conducted in a first hydrolysis reactor and the liquid residue from that may be taken to a second hydrolysis reactor in which amide and amide sulphate residues in that liquid may be subjected to hydrolysis. In particular, excess steam may be blown through the liquid in this second reactor in an amount such that some of the steam passes through the reactor and strips carboxylic acid from the reactor. This stream of steam from the second reactor advantageously is then recycled as all or part of the supply of steam to the first reactor.

Generally the reaction between the nitrile and water in the presence of sulphuric acid will have been conducted initially in a separate reactor with the reaction product from that being fed to the primary hydrolysis reactor.

It will be appreciated that although the process can be carried out as a batch process it is particularly suitable for carrying out as a continuous process. Thus the reactants are continuously fed to the reaction vessels and product acid and by-products are continuously removed from the reaction mixture.

When the acid product is driven off from the liquid reaction mixture and distilled over as a mixture with steam, the vapour may be cooled and condensed after which it may be further purified or concentrated or diluted, depending upon the desired end use.

In order to prevent polymerisation during the process a polymerisation inhibitor needs to be included in the mixture at all stages of the reaction. Conventional polymerisation inhibitors may be used. Different inhibitors may be used in different stages of the process. The preferred inhibitors include methylene blue and paramethoxyphenol.

The following examples illustrate the invention:

COMPARATIVE EXAMPLE

In a pilot trial of a continuous process, acrylonitrile (10k mole/hr), inhibitor, and 87% aqueous sulphuric acid (12 k mole/hr $H_2SO_4$ + 10k mole/hr $H_2O$) are reacted together in a stirred reactor, the temperature in the reaction mixture being maintained in the range 95°-98° C. The product mixture, comprising acrylamide sulphate (10k mole/hr) plus excess sulphuric acid (2k mole/hr), is then fed into a stirred primary hydrolysis reactor where the liquid is maintained at about 175° C. by the addition of water (approx. 50 kg/hr).

Steam at temperature of 165° C. for hydrolysis and stripping is supplied to the liquid in the primary hydrolysis reactor by introduction under the surface at a rate of about 370 kg/hr. Acrylic acid/steam product mixture (about 60% by weight acid) is driven from the reactor at a rate of about 8.7k mole/hr of acid. It is contaminated with from 100 to 300 ppm sulphur dioxide.

The reactor contents comprising mainly ammonium bisulphate and sulphuric acid are fed to a stirred secondary hydrolysis reactor which is maintained at a temperature of 165° C. Steam is added to this reactor below the surface of the liquid at a rate of about 370 kg/hr. A mixture of steam with further acrylic acid (approx. 34 kg/hr) is distilled off the mixture in the secondary reactor and passed back below the liquid surface of the primary reactor as the source of steam for the hydrolysis and stripping.

The liquid by-product mixture comprising about 10k mole/hr ammonium bisulphate and 2k mole/hr sulphuric acid plus small amounts of acrylic acid and polymer is then diluted in-line with about 550 kg/hr water and stored for disposal. The ratio of the total dry weight of sulphate by-product (ammonium bisulphate and sulphuric acid) to dry weight acrylic acid is 2.15:1.

EXAMPLE

The process of the comparative example is repeated with the same feeds of acrylonitrile, sulphuric acid and water. As the characterising step of the reaction, the water feed to the primary hydrolysis reactor is replaced by a 50% aqueous solution of acrylamide at a rate of 2.9k moles/hr.

Acrylic acid is recovered at a rate of about 11.2k moles/hr as a 60% mixture with water, and is contaminated with only about 10–15 ppm sulphur dioxide.

The liquid by-product mixture contains 11.1k mole/hr ammonium bisulphate and 0.9k mole/hr ammonium sulphate plus small amounts acrylic acid and polymer. The ratio of the total dry weight of sulphate by-product (ammonium bisulphate and ammonium sulphate) to dry weight of acrylic acid product is 1.73:1.

Thus the yield of by-product, per unit weight acrylic acid, is substantially less and the by-product is less acidic and the amount of sulphur dioxide in the acrylic acid product is much less. A further advantage is that the amount of p-methoxyphenol that had to be added to the primary hydrolysis reaction to give a concentration in the product acid in the range 200–300 ppm was reduced in the Example of the process according to the invention by 60% as compared to the Comparative Example.

We claim:

1. In a process for making an ethylenically unsaturated acid of the formula $R^1C=CR^2COOH$, in which $R^1$ is H, alkyl or aryl and $R^2$ is H or $CH_3$, from starting materials comprising the corresponding nitrile comprising feeding the nitrile to a reaction vessel and reacting it in aqueous solution in that vessel with water in the presence of an amount of sulphuric acid that is above 1 mole per mole nitrile and thereby forming a first reaction product containing the corresponding amide sulphate, hydrolysing the amide sulphate by reaction in aqueous solution with water and thereby forming the corresponding acid and a sulphate by-product, and separating the corresponding acid from the sulphate by-product, the improvement which comprises including the corresponding amide in the said starting materials and feeding the said corresponding amide into the first reaction product and hydrolysing it with the amide sulphate, in which the amount of amide fed into the reaction product is such that the total amount of amide and nitrile fed to the process is above 1 mole per mole sulphuric acid.

2. A process according to claim 1 in which $R^1$ is hydrogen.

3. A process according to claim 1 in which the nitrile is acrylonitrile, the amide is acrylamide and the acid is acrylic acid.

4. A process according to claim 1 in which the reaction of the nitrile in the presence of sulphuric acid is conducted at about atmospheric pressure at a temperature of 90° to 100° C. and the hydrolysis of the amide sulphate and amide is conducted at about atmospheric pressure and at a temperature of 160° C. to 190° C.

5. A process according to claim 1 in which at least some of the water is provided in the form of steam which is blown, during the hydrolysis of the amide sulphate, through the first reaction product in an amount such that some of the steam passes through the product and strips the acid from the reaction mixture.

6. A process according to claim 5 in which the hydrolysis of the amide sulphate and amide is conducted in a primary hydrolysis reactor and the liquid residue from this is subjected to hydrolysis in a second hydrolysis reactor and the steam is blown through the second reactor in an amount such that some of the steam passes through the reactor and strips the acid from the reactor, and in which this resultant stream of steam is recycled as all or part of the supply of steam to the first reactor.

7. A process according to claim 6 conducted continuously and in which the reaction of the nitrile in the presence of sulphuric acid is conducted in a separate reactor and the reaction product from this is fed to the first hydrolysis reactor.

8. A process according to claim 1 in which the molar ratio of nitrile to sulphuric acid is from 1:1.05 to 1:1.5 and the molar ratio of total nitrile and amide fed to the process:sulphuric acid is from 1.01:1 to 1.7:1.

9. A process according to claim 1 in which the molar ratio of nitrile to sulphuric acid is from 1:1.1 to 1:1.3 and the molar ratio of total nitrile and amide fed to the process:sulphuric acid is from 1.1:1 to 1.5:1.

10. A process according to claim 9 in which the amide is added in an amount of 0.1 to 0.4 mole above the difference between the molar proportions of sulphuric acid and nitrile.

11. A process according to claim 10 in which at least some of the water is provided in the form of steam which is blown, during the hydrolysis of the amide sulphate, through the first reaction product in an amount such that some of the steam passes through the product and strips the acid from the reaction mixture.

12. A process according to claim 11 in which the nitrile is acrylonitrile, the amide is acrylamide and the acid is acrylic acid.

13. A process according to claim 12 in which the reaction of the nitrile in the presence of sulphuric acid is conducted at about atmospheric pressure at a temperature of 90° C. to 100° C. and the hydrolysis of the amide sulphate and amide is conducted at about atmospheric pressure and at a temperature of 160° C. to 190° C.

14. A process according to claim 1 in which the amide is added in an amount of 0.1 to 0.4 moles above the difference between the molar proportions of sulphuric acid and nitrile.

15. A process according to claim 1 in which the amount of sulphuric acid is 1.05 to 1.5 moles per mole nitrile, the total amount of amide and nitrile fed to the process is 1.01 to 1.7 moles per mole sulphuric acid and the amide is added in an amount of 0.05 to 0.5 moles above the difference between the molar proportion of sulphuric acid and nitrile.

* * * * *